United States Patent [19]

Muro et al.

[11] Patent Number: 5,391,813
[45] Date of Patent: Feb. 21, 1995

[54] PROCESS FOR PRODUCING METHYL α-HYDROXYISOBUTYRATE

[75] Inventors: Nobuyuki Muro; Takafumi Abe; Hirofumi Higuchi, all of Niigata, Japan

[73] Assignee: Mitsubishi Gas Chemical Company, Inc., Tokyo, Japan

[21] Appl. No.: 135,247

[22] Filed: Oct. 12, 1993

[30] Foreign Application Priority Data

Nov. 9, 1992 [JP] Japan .................................. 4-298780

[51] Int. Cl.⁶ .......................................... C07C 69/675
[52] U.S. Cl. ................................................ 560/179
[58] Field of Search ......................................... 560/179

[56] References Cited

U.S. PATENT DOCUMENTS 4,990,651  2/1991  Ikarashi et al. ................. 560/103
5,194,668  3/1993  Ikarashi et al. ................. 560/103

FOREIGN PATENT DOCUMENTS 0413140  2/1991  European Pat. Off. .

*Primary Examiner*—José G. Dees
*Assistant Examiner*—Barbara S. Frazier
*Attorney, Agent, or Firm*—Frishauf, Holtz, Goodman & Woodward

[57] ABSTRACT

There is disclosed a process for efficiently producing methyl α-hydroxyisobutyrate from α-hydroxyisobutyramide and methyl formate by means of reaction distillation which comprises feeding α-hydroxyisobutyramide and an alkali metal hydroxide in a continuous distillation column to prepare therein the dehydrated condensate of α-hydroxyisobutyramide with the alkali metal hydroxide as the catalyst and reacting remaining α-hydroxyisobutyramide with methyl formate in the presence of the dehydrated condensate as the catalyst.

According to the above process, the objective methyl α-hydroxyisobutyrate is continuously obtained in high yield and high selectivity without any operational trouble.

19 Claims, 1 Drawing Sheet

| 5,391,813

PROCESS FOR PRODUCING METHYL α-HYDROXYISOBUTYRATE

BACKGROUND OF THE INVENTION

1. Field of the Invention

The present invention relates to a process for producing methyl α-hydroxyisobutyrate from α-hydroxyisobutyramide and methyl formate. Methyl α-hydroxyisobutyrate has industrially significant uses, for example, as a starting raw material for methyl methacrylate.

2. Description of the Related Arts

As a process for producing a carboxylic acid ester from a carboxylic acid amide, there has heretofore been known the process by reacting a carboxylic acid amide with an alcohol in the presence of sulfuric acid, which process is widely put into practice as a process for industrially producing methyl methacrylate.

However, the above-mentioned process involves the problems that a huge amount of acidic ammonium sulfate is formed as a byproduct requiring great expense for its disposal and besides expensive corrosion-resisting production facilities are needed.

As a means for solving the above-mentioned disadvantages, there is proposed a process for producing a carboxylic acid ester by reacting a carboxylic acid amide contact into an alcohol without the use of sulfuric acid. The process, however, is not industrially satisfactory because of several problems that the yield and selectivity of the objective carboxylic acid ester are limited, a large amount of ammonia is produced neccesitating its separation and recovery, and an ammonium salt of a carboxylic acid is unfavorably formed.

As a process not accompanied by the formation of ammonia, there is proposed in Japanese Patent Application Laid-Open Nos. 55444/1983 and 78937/1985, a process for producing a carboxylic acid ester and formamide by reacting a carboxylic acid amide with a formic acid ester by the use of a combined catalyst of a metallic salt of an organic acid or an inorganic acid or a metallic carbonyl compound with an organic compound containing nitrogen or phosphorus. Yet, some problems remain in the process in that the catalyst system is complicated and expensive, and great expense is required for recovering the catalyst.

The present inventors have found a process for producing a carboxylic acid ester in high selectivity which comprises reacting a carboxylic acid amide with a formic acid ester by the use of the catalyst comprising the dehydrated condensate of a carboxylic acid amide with a hydroxide of an alkali metal or an alkaline earth metal under extremely mild reaction conditions as compared with the publicly known processes, which process is disclosed in Japanese Patent Application Laid-Open No. 48637/1991. Notwithstanding the improvement, the above-mentioned process proved to have weakpoints as described hereunder as the result of further investigation. In the case of industrially producing methyl α-hydroxyisobutyrate by the above-mentioned process, it is necessary to efficiently prepare the catalyst composed of the dehydrated condensate of α-hydroxyisobutyramide with a hydroxide of an alkali metal. The preparation of the catalyst, however, is liable to be accompanied by the hydrolytic reaction of α-hydroxyisobutyramide due to the water formed at the time of dehydrative condensation, and the α-hydroxyisobutyric acid thus formed produces a salt with the alkali metal hydroxide. Consequently, the alkali metal hydroxide eventually fails to serve effectively as the catalyst. In addition, the alkali metal hydroxide is preferably used in the form of an aqueous solution from an operational convenience, which however, further accelerates the hydrolytic reaction of α-hydroxyisobutyramide, thereby causing troubles in an attempt to efficiently prepare the dehydrated condensate for the sake of the catalyst only.

SUMMARY OF THE INVENTION

It is an object of the present invention to develop a method of preparing a catalyst comprising the dehydrated condensate of α-hydroxyisobutyramide with an alkali metal hydroxide to be used for the reaction of α-hydroxyisobutyramide with methyl formate by solving the previous disadvantages.

It is another object of present invention to provide a industrial process for continuously producing methyl α-hydroxyisobutyrate from α-hydroxyisobutyramide and methyl formate by the use of the catalyst comprising the dehydrated condensate of α-hydroxyisobutyramide with an alkali metal hydroxide.

As a result of intensive research and investigation, it has been found by the present inventors that the above-described disadvantage can be solved by the steps of subjecting α-hydroxyisobutyramide and an alkali metal hydroxide to reaction distillation by the use of and inside a continuous multistage distillation column, where a dehydrative reaction and a dehydrative distillation are simultaneously carried out for preparing the dehydrated condensate as the catalyst; and reacting the bottom product in the column with methyl formate.

Specifically the present invention relates to a process for efficiently producing methyl α-hydroxyisobutyrate from α-hydroxyisobutyramide and methyl formate which comprises feeding α-hydroxyisobutyramide and an alkali metal hydroxide in a continuous distillation column to prepare therein the dehydrated condensate of α-hydroxyisobutyramide with the alkali metal hydroxide as the catalyst and reacting remaining α-hydroxyisobutyramide with methyl formate in the presence of said dehydrated condensate as the catalyst.

More specifically the present invention pertains to a process for efficiently producing methyl α-hydroxyisobutyrate from α-hydroxyisobutyramide and methyl formate which comprises the steps of (1) feeding α-hydroxyisobutyramide in a continuous distillation column at a tray positioned between the top and the bottom of the column; (2) feeding an alkali metal hydroxide in the column at a tray between the tray at which the α-hydroxyisobutyramide is fed and the bottom of the column; (3) bringing the α-hydroxyisobutyramide into contact with the alkali metal hydroxide to produce the dehydrated condensate thereof, while distilling away water from the top of the column and drawing out the remaining α-hydroxyisobutyramide and the dehydrated condensate as the bottom products from the bottom of the column; and (4) reacting the bottom product with methyl formate into methyl α-hydroxyisobutyrate.

Figure 1:
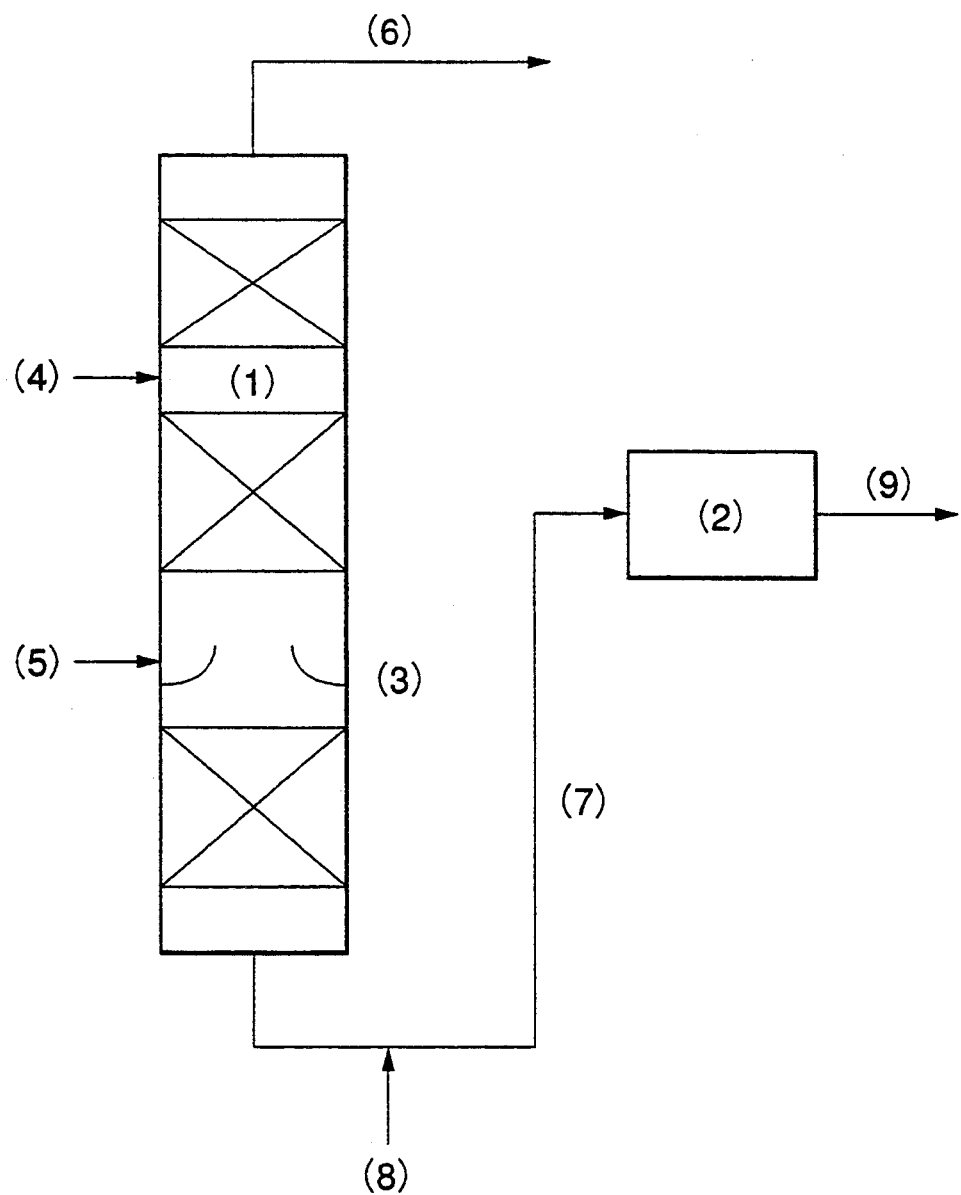
FIG. 1 illustrates the process flow diagram for carrying out the process according to the present invention. Description of the symbols therein is as follows.

(1) : dehydrative distillation column (2) : reactor
(3) : liquid reservoir
(4) : α-hydroxyisobutyramide feed line (5) : alkali metal hydroxide feed line
(6) : water drawing out line
(7) : bottom products drawing out line
(8) : methyl formate feed line
(9) : reaction liquid drawing out line

DESCRIPTION OF PREFERRED EMBODIMENT

In the process according to the present invention, the alkali metal hydroxide is fed into the multistage distillation column at a tray positioned between the feed inlet of the α-hydroxyisobutyramide and the bottom of the column. The selective feeding method as mentioned above enables the production of the objective methyl α-hydroxyisobutyrate in high yield and high selectivity, as well as the effective preparation of the catalyst, since water can instantaneously be distilled away from the top of the column and the hydrolytic reaction of α-hydroxyisobutyramide can be suppressed by the aforesaid method. On the other hand, it is unfavorable to feed the alkali metal hydroxide in the feed line of α-hydroxyisobutyramide or at the tray having a feed inlet of the same from the viewpoint of effective preparation of the catalyst because the α-hydroxyisobutyramide is hydrolyzed. Feeding the alkali metal hydroxide at the bottom of the column is also unfavorable because of insufficient water removal which leads to decrease in the production of the dehydrated condensate.

The starting raw material, that is, α-hydroxyisobutyramide to be used in the process according to the present invention is obtained by hydrating acetone cyanohydrin which is produced from acetone and prussic acid. The α-hydroxyisobutyramide contains usually a small amount of water and thus formamide which is produced by the hydration of prussic acid. Even in such a case, the catalyst can be prepared without any trouble by the method according to the present invention in which the alkali metal hydroxide is fed at a tray positioned between the feed inlet of α-hydroxyisobutyramide and the bottom of the column.

In the following, the process according to the present invention will be described in more detail with reference to FIG. 1 in which symbol (1) denotes the entire unit of distillation column.

α-Hydroxyisobutyramide is fed in the column at an intermediate tray therein through the feed line (4), alone or in combination with 0 to 50% by weight of water. At the same time, the alkali metal hydroxide is fed therein through the line (5), the feed inlet of which can be provided with the liquid reservoir (3) so as to prevent clogging due to the deposition of crystals.

Examples of the alkali metal hydroxide to be used in the present process include the hydroxide of lithium, sodium, potassium, rubidium and cesium, respectively, among which sodium hydroxide is preferable from the economical point of view. The alkali metal hydroxides can be each fed in the distillation column in the form of powder as such, but, in view of handling, preferably in the form of aqueous solution in a concentration of 5 to 30%, preferably 20 to 30% by weight in a proportion of 0.005 to 0.1 mole (0.5 to 10 mole %), preferably 0.007 to 0.08 moles (0.7 to 8 mole %) based on one mole of α-hydroxyisobutyramide. A usage thereof more than 10 mole % is pratically disadvantageous because the hydrolysis thereof is accelerated and the amount of water to be distilled away is increased thereby.

With regard to the amount of the above-mentioned alkali metal hydroxide to be fed, part of the α-hydroxyisobutyramide to be fed is substantially subjected to dehydrative reaction with the alkali metal hydroxide, resulting in the production of the mixture of the dehydrated condensate of α-hydroxyisobutyramide with the alkali metal hydroxide as the catalyst and the unreacted α-hydroxyisobutyramide as one of the starting raw materials for the objective product.

Aside therefrom, water is distilled away from the top of the column through the line (6).

The above-mentioned dehydrative condensation is caused under the operation conditions including a vacuum of 5 to 20 torr. preferably 10 to 15 torr. at a bottom temperature of 130° to 160° C., preferably 140° to 150° C., and the resultant mixture as described hereinbefore is fed in the reactor (2) from the bottom of the column through the line (7).

As mentioned above, there is produced by the reaction inside the column, the mixture of the dehydrated condensate of α-hydroxyisobutyramide with the alkali metal hydroxide as the catalyst and the unreacted α-hydroxyisobutyramide. Consequently, the catalyst and one of the starting raw materials are simultaneously fed in the reactor (2) in combination with each other.

A bottom temperature higher than 160° C. undesirably results in the liability to the distilling away or degeneration of α-hydroxyisobutyramide and decomposition of the dehydrated condensate thus formed, whereas that lower than 130° C. unfavorably leads to insufficient dehydration, thereby lowering the formation of the dehydrated condensate to be used as the catalyst.

Methyl formate as the other starting raw material is fed in the line (7) through the line (8) in a feed amount of 0.5 to 20 moles (50 to 2000 mole %), preferably 1.5 to 8 moles (150 to 800 mole %) based on one mole of α-hydroxyisobutyramide. A feed amount thereof less than 0.5 mole brings about uncommercial deterioration of the conversion efficiency, whereas that more than 20 moles gives rise to unpractical increase in the amount of unreacted methyl formate to be recovered.

It is desirable to use methanol when necessary in the handling of α-hydroxyisobutyramide in the stage of feeding methyl formate and in the stage of reacting α-hydroxyisobutyramide with methyl formate in an amount of 1 to 30 moles, preferably 2 to 20 moles based on one (1) mole of α-hydroxyisobutyramide. An amount thereof less than one (1) mole causes difficulty in dissolving α-hydroxyisobutyramide, while that more than 30 moles brings about practically disadvantageous increase in the amount of methanol to be recovered from the reaction liquid.

The mixed solution in the aforestated proportion is fed in the reactor (2), from which the objective methyl α-hydroxyisobutyrate is obtained through the line (9).

The reaction temperature and reaction time in the reactor (2) can be selected in a wide range depending on the feed amount of the alkali metal hydroxide and the aimed conversion efficiency. As the general reaction conditions, the reaction temperature is in the range of preferably 20° to 150° C., particularly preferably 30° to 100° C., and the reaction time is in the range of 0.1 to 10 hr, or 2 to 5 hours which suffices the practical application. A reaction temperature lower than 20° C. results in failure to attain a practical reaction rate, whereas that higher than 150° C. causes a disadvantage of liability to decomposition of the dehydrated condensate.

According to the process of the present invention, the objective methyl α-hydroxyisobutyrate is obtained in high yield and high selectivity through the reaction of α-hydroxyisobutyramide with methyl formate by virtue of efficiently preparing the catalyst composed of the dehydrated condensate of α-hydroxyisobutyramide with the alkali metal hydroxide by means of reaction distillation.

In the following, the present invention will be described in more detail with reference to comparative examples and an example, which however shall not be construed to limit the invention thereto.

EXAMPLE 1

A distillation column (with 20 mm inside diameter) packed inside with McMahon packings (made of stainless steel, with 6 mm size) was charged with α-hydroxyisobutyramide containing 10% by weight of water at a feed rate of 115 g/hr in the middle thereof and 30% by weight of aqueous solution of sodium hydroxide at a feed rate of 4g/hr at a position between the above feed inlet and the column bottom. Under the operational conditions including a column bottom temperature of 150° C. and a column top pressure of 10 torr., water was distilled away from the column top, and the mixture of the dehydrated condensate and unreacted α-hydroxyisobutyramide was obtained from the column bottom. To the mixture was continuously added a solution of methyl formate in methanol in a molar ratio of 2:3 at a feed rate of 216 g/hr, and the resultant mixture was fed in a reactor, where the reaction was carried out at 60° C. for a retention time of 2 hours. As a result, the conversion of α-hydroxyisobutyramide was 61% and the selectivity to methyl α-hydroxyisobutyrate was 99%.

COMPARATIVE EXAMPLE 1

The procedure in Example 1 was repeated except that the aqueous solution of sodium hydroxide was fed in the column at the tray having the feed inlet of the above α-hydroxyisobutyramide.

As a result, the conversion of α-hydroxyisobutyramide was 49% and the selectivity to methyl α-hydroxyisobutyrate was 92%.

COMPARATIVE EXAMPLE 2

The procedure in Example 1 was repeated except that the aqueous solution of sodium hydroxide was fed in the bottom of the column.

As a result, the conversion of α-hydroxyisobutyramide was 43% and the selectivity to methyl α-hydroxybutyrate was 90%.

What is claimed is:

1. A process for producing methyl α-hydroxyisobutyrate from α-hydroxyisobutyramide and methyl formate which comprises
   (a) feeding α-hydroxyisobutyramide and an alkali metal hydroxide, in a continuous distillation column having a top, a bottom and a plurality of trays therebetween, to prepare therein a dehydrated condensate of α-hydroxyisobutyramide, the alkali metal hydroxide acting as a catalyst, the α-hydroxyisobutyramide being fed into the continuous distillation column at a tray positioned between the top and the bottom of said column, the alkali metal hydroxide being fed in said column at a tray between the tray positioned at which the α-hydroxyisobutyramide is fed and the bottom of said column, the α-hydroxyisobutyramide being brought into contact with the alkali metal hydroxide to produce the dehydrated condensate thereof, while distilling away water from the top of the column and drawing out the remaining α-hydroxyisobutyramide and the dehydrated condensate as a bottom product from the bottom of said column, and
   (b) reacting said bottom product containing remaining α-hydroxyisobutyramide and said dehydrated condensate, with methyl formate, wherein said dehydrated condensate acts as a catalyst.

2. The process according to claim 1 wherein the proportion of the alkali metal hydroxide to be fed in the distillation column is 0.5 to 10 mole % based on α-hydroxyisobutyramide.

3. The process according to claim 1 wherein the alkali metal hydroxide is sodium hydroxide.

4. The process according to claim 1 wherein the alkali metal hydroxide is in the form of an aqueous solution having a concentration thereof of 5 to 30% by weight.

5. The process according to claim 1 wherein the proportion of the methyl formate fed is 50 to 2000 mole % based on α-hydroxyisobutyramide.

6. The process according to claim 1 wherein the temperature in the bottom of the distillation column is of 130° to 160° C. and the vacuum therein is of 5 to 20 torr.

7. The process according to claim 1 wherein the methyl formate is in the form of a solution of methyl formate in methanol.

8. The process according to claim 1 wherein the reaction of hydroxyisobutyramide with methyl formate is effected at a reaction temperature of 20° to 150° C. for a reaction time of 0.1 to 10 hours.

9. The process according to claim 2 wherein the alkali metal hydroxide is sodium hydroxide.

10. The process according to claim 9 wherein the sodium hydroxide is in the form of an aqueous solution having a concentration thereof of 5 to 30% by weight.

11. The process according to claim 6 wherein the temperature in the bottom of said distillation column is 130° to 160° C. and the vacuum therein is 5 to 20 torr.

12. The process according to claim 11 wherein said methyl formate is in the form of a solution of said methyl formate in methanol.

13. The process according to claim 11 wherein the reaction of said α-hydroxyisobutyramide with said methyl formate is carried out at a reaction temperature of 20° to 150° C. for a reaction time of 0.1 to 10 hours.

14. The process according to claim 12 wherein the reaction of said α-hydroxyisobutyramide with said methyl formate is carried out at a reaction temperature of 20° to 150° C. for a reaction time of 0.1 to 10 hours.

15. The process according to claim 1 wherein said alkali metal hydroxide is in the form of an aqueous solution in a concentration of 20 to 30% by weight and said alkali metal hydroxide is in an amount of 0.007 to 0.08 mole per one mole of said α-hydroxyisobutyramide.

16. The process according to claim 11 wherein said temperature is 140° to 150° C. and said pressure is 10 to 15 torr.

17. The process according to claim 11 wherein said methyl formate is fed in an amount of 150 to 800 mole % based on said α-hydroxyisobutyramide, 18. The process according to claim 7 wherein said methanol is in an amount of 2 to 20 moles based on one mole of said α-hydroxyisobutyramide.

19. The process according to claim 13 wherein said reaction temperature is 30° to 100° C. and said reaction time is 2 to 5 hours.

* * * * *

UNITED STATES PATENT AND TRADEMARK OFFICE
CERTIFICATE OF CORRECTION

PATENT NO. : 5,391,813

DATED : February 21, 1995

INVENTOR(S) : MURO et al

It is certified that error appears in the above-identified patent and that said Letters Patent is hereby corrected as shown below:

Column 6, line 36 (Claim 11):  delete "claim 6" and insert --claim 5--.

Signed and Sealed this

Twentieth Day of August, 1996

Attest:

BRUCE LEHMAN

*Attesting Officer*    *Commissioner of Patents and Trademarks*